United States Patent
Jiang et al.

(10) Patent No.: US 11,129,776 B2
(45) Date of Patent: *Sep. 28, 2021

(54) COMPOSITIONS FOR COSMETIC RAW MATERIAL AND METHODS FOR MAKING THE SAME

(71) Applicant: KPT LTD., Cheongju-Si (KR)

(72) Inventors: Yanfu Jiang, Yongin-si (KR); Ik Joo Lee, Ansan-si (KR); Woon Jang Lee, Cheongju-si (KR); Byung-ho Park, Cheongju-si (KR); Jae Uk Lee, Daejeon (KR)

(73) Assignee: KPT LTD., Cheongju-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/570,095

(22) PCT Filed: Apr. 30, 2015

(86) PCT No.: PCT/IB2015/053183
§ 371 (c)(1),
(2) Date: Oct. 27, 2017

(87) PCT Pub. No.: WO2016/174504
PCT Pub. Date: Nov. 3, 2016

(65) Prior Publication Data
US 2018/0140517 A1    May 24, 2018

(51) Int. Cl.
*A61K 8/11* (2006.01)
*A61K 8/29* (2006.01)
(Continued)

(52) U.S. Cl.
CPC ............... *A61K 8/11* (2013.01); *A61K 8/025* (2013.01); *A61K 8/0254* (2013.01); *A61K 8/29* (2013.01);
(Continued)

(58) Field of Classification Search
CPC . A61K 8/11; A61K 8/732; A61K 8/29; A61K 8/345; A61K 8/0254; A61K 8/8152;
(Continued)

(56) References Cited

U.S. PATENT DOCUMENTS

| 2006/0165620 A1* | 7/2006 | Bujard | A61K 8/11 |
| | | | 424/63 |
| 2009/0311295 A1* | 12/2009 | Mathiowitz | A61K 8/11 |
| | | | 424/401 |

(Continued)

FOREIGN PATENT DOCUMENTS

| EP | 2823804 A1 | 1/2015 |
| EP | 2939655 A1 | 11/2015 |

(Continued)

OTHER PUBLICATIONS

International Search Report and Written Opinion for International Application No. PCT/IB2015/053183 (16 Pages) (dated Oct. 22, 2015).

(Continued)

*Primary Examiner* — Robert A Wax
*Assistant Examiner* — Quanglong N Truong
(74) *Attorney, Agent, or Firm* — Lucas & Mercanti, LLP

(57) ABSTRACT

The instant invention relates to a composition for cosmetic raw material containing microcapsule containing at least one encapsulated material comprising at least one core and at least one layered coating surrounding said core, and the encapsulated material being at least one reflective particle. The invention further relates to a process for preparing the composition for cosmetic raw material containing microcapsule containing at least one encapsulated material comprising at least one core and at least one layered coating surrounding said core, and the encapsulated material being at least one reflective particle.

6 Claims, 1 Drawing Sheet

(51) Int. Cl.
    *A61K 8/34*     (2006.01)
    *A61K 8/55*     (2006.01)
    *A61K 8/73*     (2006.01)
    *A61K 8/81*     (2006.01)
    *A61K 8/02*     (2006.01)
    *A61Q 19/00*     (2006.01)
    *A61K 8/49*     (2006.01)
    *B01J 13/04*     (2006.01)
    *B01J 13/22*     (2006.01)
    *A61Q 1/02*     (2006.01)

(52) U.S. Cl.
CPC ............ *A61K 8/345* (2013.01); *A61K 8/4986* (2013.01); *A61K 8/553* (2013.01); *A61K 8/731* (2013.01); *A61K 8/732* (2013.01); *A61K 8/8152* (2013.01); *A61Q 1/02* (2013.01); *A61Q 19/00* (2013.01); *B01J 13/04* (2013.01); *B01J 13/22* (2013.01); *A61K 2800/41* (2013.01); *A61K 2800/412* (2013.01); *A61K 2800/43* (2013.01); *A61K 2800/63* (2013.01)

(58) Field of Classification Search
CPC ...... A61K 8/731; A61K 8/553; A61K 8/4986; A61K 2800/41; A61K 2800/412; A61K 2800/43; A61K 2800/63; A61Q 19/00; A61Q 1/02
See application file for complete search history.

(56) References Cited

U.S. PATENT DOCUMENTS

2012/0237578 A1*   9/2012   Lei .................... B01J 13/206
                                                                                       424/401
2017/0143597 A1*   5/2017   Jiang ..................... A61Q 19/00

FOREIGN PATENT DOCUMENTS

| WO | 2004041991 A1 | 5/2004 | |
| WO | 2013/107354 A1 | 7/2013 | |
| WO | 2013107001 A1 | 7/2013 | |
| WO | 2013108410 A1 | 7/2013 | |
| WO | WO-2013107350 A1 * | 7/2013 | ............... A61Q 1/06 |
| WO | 2015004630 A1 | 1/2015 | |

OTHER PUBLICATIONS

The extended European search report, Application No. 15890676.8, dated Nov. 13, 2018.

* cited by examiner

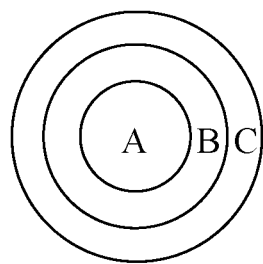

COMPOSITIONS FOR COSMETIC RAW MATERIAL AND METHODS FOR MAKING THE SAME

CROSS-REFERENCE TO RELATED APPLICATIONS

This application is a 371 of PCT/IB2015/053183, filed Apr. 30, 2015, the content of which is incorporated herein by reference.

FIELD OF THE INVENTION

The present invention relates to compositions for cosmetic raw material comprising microcapsules containing at least one reflective particle, and methods for making the same.

BACKGROUND OF THE INVENTION

There is a growing interest in imparting care properties in cosmetic products especially in make-up compositions. These care properties are often associated with a smooth, creamy, rich appearance of the compositions.

Nevertheless, the introduction of some ingredients in cosmetic compositions may be detrimental towards the general appearance and comfort of use of the composition, in particular for skin-care products for which it is generally sought some codes which are an aesthetical purity of the composition associated with a good texture when the composition is picked up and applied onto the skin.

In particular, the introduction of some ingredients in cosmetic compositions may be detrimental towards the homogeneity of the composition with respect to the presence of such ingredients which may then be inhomogeneously dispersed typically when they are in the form of particles. And even the introduction of some ingredients may sometimes induce additional problems attached to this dispersion problem, such as the thickening of the composition, modification of the composition appearance when the ingredients are colored or exhibit iridescence. As far as such additional optical effects, for example in connection to the presence of reflective particles, are not necessary desired, there exists a need to reduce such drawbacks.

As representative of this kind of ingredient may in particular be reflective particles.

Moreover, some of them absorb a significant part of the composition in which they are introduced, this absorption leading to a thickening of the composition which may be undesirable.

Reflective particles are furthermore mainly used for their visual properties, particularly for the sparkle, glitter, or pearly effect they can confer to the composition and also to the users when applied.

Nevertheless a major technical problem with reflective particles is to obtain a homogeneous composition that is a composition wherein the reflective particles are uniformly distributed.

Indeed the reflective particles tend to migrate at the composition interfaces during the storage, namely at the surface and against the inside of the container wall.

This phenomenon may sometimes be desired, but homogenous compositions are generally preferred.

Accordingly, there is a need for compositions containing such reflective particles but wherein the reflective particles are homogenously distributed.

Surprisingly and advantageously, the compositions according to the invention meet these needs. Moreover, compositions according to the invention act favorably with respect to desired optical effects on the skin, namely radiance and evenness.

SUMMARY OF INVENTION

The present invention provides compositions for cosmetic raw material comprising microcapsules containing at least one reflective particle.

The microcapsules according to the invention are particularly interesting for the following reasons.

The encapsulated reflective particles are kept in the microcapsules during the storage of the composition and only released upon application of said composition on the keratin material.

By this way, the microcapsules according to the invention are able to permanently retain the reflective particles in the microcapsule during storage of the composition, and thus efficiently prevent any undesirable modification of the stability of the composition and to keep a same long-term visual effect to said composition.

Particularly, the reflective particles either appear to be uniformly distributed in the composition or are not visible in the bulk. But in both cases, the composition is visually homogeneous.

By using said microcapsules, it is possible to achieve cosmetic compositions containing greater amount of reflective particle(s).

By this way, the microcapsules according to the invention allow to overcome incompatibility issues due to the use of reflective particle(s) with other ingredient(s) of the composition.

The microcapsules according to the invention are also advantageously stable with a large panel of solvent/ingredient associated.

They are also stable in the compositions according to the present invention, preferably at high temperatures, for instance greater than or equal to 40° C., for example for one month, better two months and still better three months in an oven at 45° C. or for 15 days in an oven at 60° C.

In a preferred embodiment, the microcapsules according to the present invention present appropriate softening kinetics.

That is preferably, at least three hours after being in contact with the other compounds of the formula, the hardness of the microcapsules is advantageously from 5 to 50 grams, more preferably from 6 to 20 grams and still more preferably from 7 to 10 grams. Such hardness is in conformity with an industrial process for preparing the cosmetic compositions including such microcapsules.

Such values of softening kinetics and hardness allow to provide not only aesthetic microcapsules but also overall aesthetic compositions.

Further some reflective particles, particularly nacres, may also lead to changing color compositions. Namely the encapsulated reflective particles may confer a color to the composition which is different from the color obtained after application of the composition, i.e., after the microcapsules containing reflective particles have been broken.

Advantageously, they have the ability of swelling or softening in contact of a liquid medium such as water and optionally at least one compound chosen from polyols, glycols and $C_2$-$C_8$ monoalcohols, and mixtures thereof, or alternatively in a liquid fatty phase (preferably an oily phase). By this way, they are advantageously deformable when applied on a keratin material and consequently provide a soft feeling to the user.

Furthermore, their size contributes to not create any discomfort or unfavorable, grainy feeling when applied. In particular, they are soft enough to rupture upon very slight rubbing or pressing on the skin in order to release their content.

They disintegrate rapidly immediately when applied, with a liquid feeling on the skin and leading to compositions devoid of any granular aspect.

However, they are durable enough to avoid destruction of the coating during manufacture, even during an industrial process, and storage of corresponding composition. Thus, they exhibit hardness sufficient to be compounded in an industrial process without alteration. Advantageously the hardness of the microcapsules does not significantly decrease during the preparation process. Thus, they allow the use of regular equipment for the preparation of the compositions of the invention.

Accordingly, the microcapsules of the present invention are particularly interesting since they increase the stability of the reflective particle against degradation, and prevent undesirable release of the encapsulated actives into the composition during the manufacturing process and prolonged storage.

Another aspect of the present invention is a process of preparing the microcapsules. The process includes:

preparing an aqueous solution containing water and a first hydrophilic polymer;

dispersing reflective particles in the aqueous solution;

forming an inner layer on a core with the aqueous solution in which the reflective particles are dispersed;

forming an intermediate layer on the inner layer with an intermediate layer solution containing water, a second hydrophilic polymer, and a pigment; and forming an outer layer on the intermediate layer with an outer layer solution containing water and a third hydrophilic polymer.

BRIEF DESCRIPTION OF THE DRAWINGS

FIG. 1 is a schematic diagram illustrating a typical structure of a microcapsule of the present invention wherein A represents a core and B, and C, being different layers concentrically surrounding said core.

FIG. 1 typically represents the microcapsule of example 12 wherein A represents the core comprising lecithin, mannitol, a corn starch binder and reflective particle(s), B represents the inner layer comprising lecithin, mannitol, a corn starch binder and reflective particle(s) and C represents the outer layer comprising lecithin and a corn starch binder.

DETAILED DESCRIPTION OF THE INVENTION

A composition according to one aspect of the invention may comprise from 0.1% to 20% by weight and preferably from 0.5% to 15% by weight of microcapsules relative to the total weight of the said composition.

In particular for a skin care composition according to the invention, the amount of microcapsules will range from 0.1% to 5%, preferably from 0.2% to 3% by weight relative to the total weight of composition.

In particular for a make-up composition according to the invention, the amount of microcapsules will range from 0.5% to 30%, preferably from 1% to 15%, more preferably from 2% to 10% by weight relative to the total weight of composition.

Advantageously, in certain aspects the ratio between the microparticle volume and the composition volume ranges from 10 to 95.

Advantageously, a composition of the invention may comprise two or more microcapsules of the invention different from each other.

According to a first embodiment, the encapsulated reflective particle(s) is/are present in the core of the microcapsules. Particularly, the encapsulated reflective particle(s) is/are only present in the core of the microcapsules.

In on specific sub-embodiment, the core of said microparticles includes at least one or several reflective particles and at least one binder.

In another specific sub-embodiment, the reflective particle(s) is/are present in the core as a lipidic or aqueous dispersion.

According to a second embodiment, at least one inner layer surrounding the core includes the reflective particle(s).

Inner layer means that this layer is obligatory surrounded by another inner or outer layer. Further the layered coating advantageously comprises at least one inner layer and one outer layer.

Particularly, the encapsulated reflective particle(s) is/are only present in at least one inner layer of the microcapsules.

The term "encapsulated" means that the reflective particle is always entrapped inside the microcapsules according to the invention.

In other words, the outer layer of the microcapsules encapsulating the reflective particle is always free from any reflective particle. Advantageously, the outer layer is free from reflective particle(s) and preferably comprises at least one hydrophilic polymer and optionally a binder. Such a binder, i.e. a hydrophilic polymer, may be selected from hydrophilic polymer such as starch, cationic starch, cellulose, modified cellulose, Mannitol, sucrose, polyvinyl alcohol and Carrageenan.

According to a third embodiment, the encapsulated reflective particle is present in the core of the microcapsules and in at least on inner layer.

Chemical Nature of Microcapsules

According to a preferred embodiment, the core is an organic core.

The core of the microparticles may consist in at least one or several reflective particles. If the core is not totally made of reflective particles, it comprises additional organic material(s).

Advantageously the core represents from 1% to 50% by weight, preferably 5 to 30% by weight, and in particular from 10 to 20% by weight relative to the total weight of the microcapsule.

Preferably the microcapsules have a double layer surrounded the core.

Preferably, the microcapsules contain at least one organic layer, preferably one inner organic layer.

According to a preferred embodiment, the microcapsules contain at least one layer, preferably at least one inner layer, comprising at least one binder.

According to another embodiment the outer layer comprises a binder.

Advantageously, the microcapsules have a size of from 50 μm to 800 μm, in particular from 60 μm to 600 μm, and in particular from 80 μm to 500 μm, and in particular from 100 μm to 400 μm.

Preferably the microcapsule comprises at least 5%, preferably at least 10%, more preferably at least 30%, better at least 40%, even better at least 50%, advantageously at least 60% and in particular between 30 and 80% preferably between 40 and 75% by weight of reflective particle(s) relative to the weight of the microcapsule.

According to a preferred embodiment, the microcapsules comprise:
- a core comprising at least one reflective particle and optionally at least one additional organic material,
- at least one layered coating surrounding said core, the layered coating comprising a binder selected from at least one polymer, at least one lipid-based material, and their mixture, preferably their mixture and optionally at least one reflective particle,
- an outer layer comprising a hydrophilic polymer.

According to another preferred embodiment, the microcapsules comprise
- a core comprising at least one organic material,
- at least one layered coating surrounding said core, the layered coating comprising a binder selected from at least one polymer, at least one lipid-based material, and their mixture, preferably their mixture and at least one reflective particle,
- an outer layer comprising a hydrophilic polymer.

Preferably, the core comprises at least one monosaccharide or its derivatives as said organic material, in particular a monosaccharide-polyol advantageously selected from mannitol, erythritol, xylitol, sorbitol and mixtures thereof, preferably mannitol.

Preferably, the layered coating surrounding said core comprises at least one hydrophilic polymer(s) selected from the group consisting of:
- acrylic or methacrylic acid homopolymers or copolymers or salts and esters thereof;
- copolymers of acrylic acid and of acrylamide and its salts and esters thereof;
- polyhydroxycarboxylic acids and its salts and esters thereof;
- polyacrylic acid/alkyl acrylate copolymers, preferably modified or unmodified carboxyvinyl polymers;
- AMPS;
- AMPS/acrylamide copolymers;
- polyoxyethylenated AMPS/alkyl methacrylate copolymers;
- anionic, cationic, amphoteric or nonionic chitin or chitosan polymers;
- cellulose polymers and derivatives;
- Starch polymers and derivatives, eventually modified;
- vinyl polymers and derivatives;
- polymers of natural origins and derivatives thereof;
- alginates and carrageenans;
- glycoaminoglycans, hyaluronic acid and derivatives thereof;
- mucopolysaccharides such as hyaluronic acid and chondroitin sulfates;
- and the mixtures thereof.

Advantageously the layered coating comprises at least hydrophilic polymer(s) selected from the group consisting of polysaccharides and derivatives, acrylic or methacrylic acid homopolymers or copolymers or salts and esters thereof, and their mixture; the polysaccharides and derivatives are preferably selected from chitosan polymers, chitin polymers, cellulose polymers, starch polymers, galactomannans, alginates, carrageenans, mucopolysaccharides, and their derivatives, and the mixture thereof, more preferably starch polymers and derivatives, cellulose polymers and derivatives, and their mixture.

Particularly the hydrophilic polymer(s) is selected from the polysaccharides and derivatives including one type of ose or several types of ose(s), preferably several types of ose(s) including at least D-glucose units.

Particularly the hydrophilic polymer is selected from starch or derivatives, celluloses or derivatives, preferably starch or derivatives.

Preferably, the core comprises at least one monosaccharide polyol, preferably selected from mannitol, erythritol, xylitol, sorbitol, and the layered coating comprises at least one polysaccharides (or its derivatives) including as oses at least D-Glucose unit(s), preferably selected from starch or derivatives, celluloses or derivatives, preferably starch or derivatives.

Preferably the outer layer of microcapsule is free from reflective particle and preferably comprises at least one hydrophilic polymer and optionally a binder.

Preferably the outer layer comprising at least one hydrophilic polymer defined in the above list. Preferably this hydrophilic polymer is at least one wall-forming polymer preferably selected from polysaccharides such as cellulose derivatives, in particular cellulose ether and cellulose ester, from (poly)(alkyl)(meth)acrylic acid and derivatives, notably (poly)(alkyl)(meth)acrylate and derivatives, and preferably from alkylacrylic/alkylmethacrylic acid copolymers and their derivatives.

Preferably, the microcapsules include at least one lipid based material, preferably with amphiphilic properties such as lecithins and in particular hydrogenated lecithin.

For the purposes of the present invention, the term "keratin material" is intended to cover the skin, mucous membranes such as the lips, the nails and the eyelashes. The skin and the lips, in particular facial skin, are most particularly considered according to the invention.

I. Microcapsules

The term "microcapsule", as used herein, refers to a spherical microcapsule containing at least one layered coating and surrounding a core chemically different from the coating. Microcapsules are distinct from microspheres, which consist of spherical homogeneous matrix.

According to an embodiment, the "at least one layered coating" is a multi-layered coating preferably an organic multi-layered coating.

The term "multi-layer microcapsule" refers to a microcapsule consisting of a core surrounded by a coating based on one or more inner layer(s) and one outer layer. The one or more inner layer(s) forming the multi-layer coating of the multi-layer microcapsule and the single outer layer of the microcapsule may be formed of the same or different wall-forming organic compound(s).

The microcapsule according to the invention comprises a core also called "inner core" surrounded by a coating based on one or more layer(s). In a preferred embodiment, the microcapsule is a 'multi-layers' microcapsule, comprising at least one inner layer and one outer layer. The one or more inner layer(s) forming the multi-layer coating of the multi-layer microcapsule and the single outer layer of the microcapsule may be formed of the same or different wall-forming organic compound(s).

In a particular embodiment the inner layer and the outer layer are formed of the same wall forming organic compounds, the core is then surrounded by a one layer coating.

The term "wall-forming organic compound" refers to an organic compound or a combination of two or more different organic compounds as defined herein, which form a component of the layer(s) of the microcapsules. In a preferred embodiment, the 'wall-forming organic compound' comprises at least one polymer.

Generally, average particle sizes of up to about 800 µm in diameter of microcapsules are used according to the invention. Preferably the average particle size is less than about 400 µm in diameter of the microcapsules for skin care applications. Advantageously the average particle size is in the range of about 10 µm to 350 µm in diameter. Preferably, the average particle size will be from 50 µm to 800 µm, in particular from 60 µm to 600 µm, and in particular from 80 µm to 500 µm, and in particular from 100 µm to 400 µm in diameter.

In particular, the average particle size may be from 50 to 1,000 Mesh (around 400 µm to 10 µm), in particular from 60 to 200 Mesh (around 250 µm to 75 µm) as measured by the sieving test method or observed by microscope.

Ia) Core

The core is made of reflective particle and/or of at least an organic material. The size of said core preferably ranges from 500 nm to 150 µm in diameter.

Preferably the core is in a solid and/or crystal form at room temperature.

In a particular embodiment, the organic material is selected from organic materials having high water dissolvability. Preferably, the core is water-soluble or water-dispersible.

In a particular embodiment, the core is based on only one compound, preferably one organic compound.

This compound may be one reflective particle.

This compound may be a natural compound.

According to a preferred embodiment, the core is sugar-alcohol, preferably a monosaccharide-polyol advantageously selected from mannitol, erythritol, xylitol and sorbitol.

In a particular embodiment, the core is made of mannitol and more preferably exclusively made of mannitol.

According to an alternative embodiment, the core contains at least mannitol and at least one additional ingredient being preferably a polymer selected from hydrophilic polymers. In particular, such a core may comprise mannitol and hydrophilic polymers chosen among cellulose polymers, starch polymers and their mixture, preferably their mixture.

In a preferred embodiment, the cellulose polymer is a carboxymethylcellulose and the starch polymer is a non-modified natural starch, for example corn starch.

The core may be constituted by a seed (or crystal) of one of the previous materials.

The core is preferably contained in an amount of from 1% to 50% by weight, preferably 4 to 40% by weight, in particular 5 to 30% by weight, and in particular from 10 to 20% by weight with respect to the total weight of the microcapsule.

The mannitol is preferably contained in an amount of from 2% to 100% by weight, preferably 5 to 100% by weight, and in particular 100% by weight with respect to the total weight of the core.

The mannitol is preferably contained in an amount of from 1% to 50% by weight, preferably 4% to 40% by weight, in particular 5% to 30% by weight, and in particular from 10% to 20% by weight with respect to the total weight of the microcapsule.

Ib) External Layer(s) or Coating

As disclosed previously, the core is advantageously surrounded with a coating, or external layer(s) preferably comprising at least one inner layer and one outer layer. In this latter case, these layers preferably extend concentrically in respect with the core.

The layer(s) is/are preferably organic, i.e. contain(s) at least one organic compound as wall-forming material. Preferably, the inner and/or outer layer(s) include(s) at least one polymer, and in particular a hydrophilic polymer.

Polymer(s)

The composition according to the invention comprises one or more polymer(s). In a particular embodiment, the polymer(s) is/are hydrophilic polymer(s).

Such hydrophilic polymer(s) is/are soluble or dispersible in water or in alcohol compounds, in particular chosen from lower alcohols, glycols, polyols.

For the purposes of the present patent application, the term "hydrophilic polymer" means a (co)polymer that is capable of forming hydrogen bond(s) with water or alcohol compounds, in particular chosen from lower alcohols, glycols, polyols. In particular, polymers are concerned which are capable of forming O—H, N—H and S—H bonds.

According to a particular embodiment of the invention, the hydrophilic polymer may swell or soften in contact with water or alcohol compounds, in particular chosen from lower alcohols, glycols, polyols.

The hydrophilic polymer(s) may be chosen from the following polymer(s):

acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company;

copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel;

polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10\text{-}30}$ Alkyl acrylate Crosspolymer) such as the products sold by the company Lubrizol under the trade names Pemulen TR1, Pemulen TR2, Carbopol 1382 and Carbopol ETD 2020, and even more preferentially Pemulen TR-2;

alkylacrylic/alkylmethacrylic acid copolymers and their derivatives notably their salts and their esters, such as the copolymer of ethyl acrylate, methyl methacrylate and low content of methacrylic acid ester with quaternary ammonium groups provided under the tradename of EUDRAGIT RSPO from Evonik Degussa;

AMPS (polyacrylamidomethylpropanesulfonic acid partially neutralized with aqueous ammonia and highly crosslinked) sold by the company Clariant;

AMPS/acrylamide copolymers such as the products Sepigel or Simulgel sold by the company SEPPIC, especially a copolymer of INCI name Polyacrylamide (and) C13-14 Isoparaffin (and) Laureth-7;

polyoxyethylenated AMPS/alkyl methacrylate copolymers (crosslinked or non-crosslinked) of the type such as Aristoflex HMS sold by the company Clariant;

polysaccharides and derivatives, such as:

anionic, cationic, amphoteric or nonionic chitin or chitosan polymers;

cellulose polymers and derivatives, preferably other than alkylcellulose, chosen from hydroxyethylcellulose, hydroxypropylcellulose, hydroxypropylmethylcellulose, hydroxymethylcellulose, ethylhydroxyethylcellulose and carboxymethylcellulose, and also quaternized cellulose derivatives; in a preferred embodiment, the cellulose polymers is a carboxymethylcellulose;

starch polymers and derivatives, eventually modified; in a preferred embodiment, the starch polymer is a natural starch;

optionally modified polymers of natural origin, such as galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;

alginates and carrageenans;

glycoaminoglycans, hyaluronic acid and derivatives thereof;

mucopolysaccharides such as hyaluronic acid and chondroitin sulfates, and mixtures thereof;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

and the mixtures thereof.

Preferably, the composition according to the invention, and in particular the external layer(s) comprise(s) hydrophilic polymers selected from the group consisting of polysaccharides and derivatives, acrylic or methacrylic acid homopolymers or copolymers or salts and esters thereof, and their mixture.

The said polymer(s) is (are) advantageously selected from (poly)(alkyl)(meth)acrylic acid and derivatives, notably (poly)(alkyl)(meth)acrylate and derivatives, preferably from alkylacrylic/alkylmethacrylic acid copolymers and their derivatives, and most preferably is a copolymer of ethyl acrylate, methyl methacrylate and low content of methacrylic acid ester with quaternary ammonium groups provided under the tradename of EUDRAGIT RSPO from Evonik Degussa.

Said polysaccharides and derivatives are preferably selected from chitosan polymers, chitin polymers, cellulose polymers, starch polymers, galactomannans, alginates, carrageenans, mucopolysaccharides, and their derivatives, and the mixture thereof.

In a preferred embodiment, the external layer(s) is/are devoid of microcrystalline cellulose.

According to one particularly preferred embodiment, said polysaccharides and their derivatives are preferably selected from the ones including one type of ose or several types of ose(s), preferably several types of oses, in particular at least D-Glucose unit(s) as ose(s), preferably starch polymers, cellulose polymers, and derivatives, and the mixture thereof.

According to a preferred embodiment, the microcapsule contains at least one hydrophilic polymer selected from the group consisting of starch and its derivatives, in particular corn starch, cellulose and its derivatives, homo- and/or co-polymer of methacrylic acid and/or methacrylic acid ester or co-polymer of (alkyl)acrylic acid and/or (alkyl) methacrylic acid and their derivatives, preferably their salts and their ester, and in particular the capsule contains polymethyl methacrylate.

Starch usable according to the present invention is usually issued from vegetable raw materials, such as rice, soybeans, potatoes, or corn. Starch can be unmodified or (by analogy with cellulose) modified starch. In a preferred embodiment, the starch is unmodified.

Preferred homo- and/or co-polymer of methacrylic acid and/or methacrylic acid ester are those wherein the copolymer of methyl methacrylate and ethyl acrylate has a molecular weight from 750 to 850 kDa.

Cellulose derivatives include, for example, alkali celluloses carboxymethyl cellulose (CMC), cellulose esters and ethers, and aminocelluloses. In a particular embodiment, the cellulose is a carboxymethyl cellulose (CMC).

According to a preferred embodiment, the capsule contains at least starch derivative, in particular corn starch, polymethyl methacrylate, co-polymer of (alkyl)acrylic acid and/or (alkyl)methacrylic acid and their derivatives preferably their salts and their ester, and/or cellulose derivative.

Preferably, the microcapsule contains polymer(s) which are not cross-linked.

The polymer(s) may be in one or several layer(s).

In another embodiment, the polymer(s) may be in the core.

The microcapsule may contain polymer(s) in the core and/or in the layer(s).

In a particular embodiment, the polymer(s) is (are) in the core and in the layer(s).

In an embodiment, the core contains at least starch and/or cellulose derivative as polymer(s). When the starch is contained within the core, it represents the main ingredient of such a core, i.e. the weight amount of starch is greater than the respective amount of other compounds of the core.

The polymer may represent from 0.5 to 20% by weight of the microcapsule, in particular from 1 to 10% by weight, preferably from 2 to 8% by weight of the microcapsule.

The different layers forming the coating may be based on identical or different polymers. Advantageously, they will be formed from the same polymer.

The microcapsules advantageously comprises at least:

a core made of at least one reflective particle and or a monosaccharide-polyol, preferably mannitol, at least two different layers, at least one hydrophilic polymer preferably selected from polysaccharide or derivatives, and more preferably from starch or derivatives, and advantageously at least one lipid based material, preferably an amphiphilic compound, more preferably a phospholipid, even more preferably phosphoacylglycerol such as hydrogenated lecithin.

Lipid-Based Material

The inner and/or outer layer(s) may also include advantageously at least one lipid-based material.

According to a particular embodiment of this invention, such a lipid-based material may have amphiphilic properties, that is to say having an apolar part and a polar part.

Such lipid-based material can include at least one or several $C_{12}$-$C_{22}$ fatty acid chain(s) such as those selected from stearic acid, palmitic acid, oleic acid, linoleic acid, linolenic acid, etc., and mixtures thereof. Preferably these fatty acids chains are hydrogenated. Eventually, these fatty acid chains may be the apolar part of a lipid-based material.

Such lipid-based material is preferably selected from phospholipids. These phospholipids are preferably selected from phosphoacylglycerol, more preferably selected from lecithins, and are in particular hydrogenated lecithin.

The lipid based material may represent from 0.05 to 5% by weight of the microcapsule, in particular from 0.1 to 1% by weight of microcapsule.

By combining three or more compounds (ex: sugar alcohols, polymers, lipid-based material) in the microcapsule of different hardness and/or water solubility, it is possible to adjust the time required for reflective particle-encapsulated microcapsules to break down on the skin. Thus, according to a preferred embodiment, the multi-layer coating contains at least starch as polymer and at least one lipid-based material, which is preferably lecithin.

According to an advantageous embodiment the microcapsules according to the invention include at least one monosaccharide or its derivative and at least one polysaccharide or its derivatives.

According to a preferred embodiment, the microcapsules include a core comprising a monosaccharide derivative and a coating comprising a polysaccharide (or its derivative) including one type of ose or several types of ose(s), preferably several types of oses.

According to a more preferably embodiment, the microcapsules include a core comprising a monosaccharide polyol, preferably selected from mannitol, erythritol, xylitol, sorbitol, and a coating comprising a polysaccharide (or its derivative) including as ose(s) at least one or more D-Glucose unit(s).

According to a preferred embodiment, the microcapsules additionally include a lipid-based material chosen from phospholipids, advantageously selected from phosphoacylglycerol and in particular from lecithins.

In a particular embodiment, the core contains mannitol, starch polymer and cellulose derivatives and optionally a lipid-based material. In such a case, the starch polymer is the main ingredient i.e. the weight amount of starch is greater than the respective amount of mannitol, cellulose derivative and lipid-based material of the core.

According to a particular embodiment of the invention, the microcapsules comprise at least:

a core comprising at least one reflective particle, a monosaccharide-polyol, preferably mannitol, a lipid based material preferably lecithin and a hydrophilic polymer preferably starch, an inner layer comprising starch as a binder, a polymer selected form alkylacrylic/alkylmethacrylic acid copolymers and their derivatives, a lipid based material preferably hydrogenated lecithin, a plasticizer, microcrystalline cellulose, hydroxypropylcellulose and optionally at least one reflective particle which may be the same or different from the reflective particle contained ion the core, an outer layer comprising TiO2, a polymer preferably selected form alkylacrylic/alkylmethacrylic acid copolymers and their derivatives and a optionally a binder preferably starch.

According to another particular embodiment of the invention, the microcapsules comprise at least:

a core comprising at least one, a monosaccharide-polyol, preferably mannitol, a lipid based material preferably lecithin and a hydrophilic polymer preferably starch, an inner layer made of comprising at least one reflective particle which may be the same or different from the reflective particle contained in the core, a monosaccharide-polyol, preferably mannitol, a lipid based material preferably hydrogenated lecithin, an outer layer made of a lipid based material preferably hydrogenated lecithin and a hydrophilic polymer preferably starch.

Reflective Particles

According to a particular embodiment, microcapsules used in the present invention comprise reflective particles in the form of flakes, more particularly having a ratio d/e greater than 10.

Reflective particles used in the present invention preferably have a refracting index greater or equal to 1.8. This allows to confer a light effect and radiance upon microcapsule rupture at the time of application of the composition.

The expression <<particles in the form of flakes>> means particles in a plate form. This means that these particles have a greatest dimension called <<d>> and a thickness called <<e>>, the ratio between the greatest dimension and the thickness of the particles that is "d/e" being greater than 10, preferably greater than 20, for example greater than 50.

The particles may have at least one plane face, or may have a radius of curvature that is greater than or equal to 60 μm. This may make it easier to stack the particles and to increase their specular reflective power.

A greatest dimension of the particles, whatever their shape, may lie in the range 5 μm to 100 μm, more preferably still in the range 10 μm to 60 μm. The size of the particles is preferably greater than or equal to 10 μm, better greater than or equal to 20 μm, still better greater than or equal to 40 μm.

The form factor "d/e" of said particles is advantageously greater than or equal to 10, better greater than or equal to 20, still better greater than or equal to 50.

Reflective particles in the form of flakes are preferably relatively monodispersed with regard to their greatest cross dimension, less or more 30%. This makes the particle deposit easier. Preferably their surface is regular, non-rough.

Measuring the Reflective Power of the Reflective Particles

The particles of reflective power that is to be measured is applied in uniform manner, at a rate of 0.2 milligrams per square centimeter ($mg/cm^2$), on a surface made of black Bioskin®, sold by Beaulax.

The reflective power is measured with the GP-5 goniophotometer sold by Murakami. The angle of incidence is fixed at −45°, and the reflectance is measured over the range −90° to 90°. The reflectance maximum, corresponding to specular reflectance, is generally measured at 45°, and it is marked $R_{45}$. The reflectance minimum, corresponding to diffuse reflectance, is generally measured at −30°, and it is marked $R_{30}$.

The reflective power of the particles is defined by $R_{45}/R_{30}$.

The reflective power of the particles of the invention, may preferably be greater than 5, more preferably greater than 7, and better greater than 10.

The reflective particles, in particular particles in the form of flakes, are present at a content that is greater than or equal to 5% by weight, preferably greater than or equal to 10% by weight, better greater than or equal to 20% by weight, ETC and better still greater than or equal to 60% by weight, relative to the total weight of the powder composition, for example ranging from 10 to 90%, by weight relative to the total weight of the microcapsule.

According to a preferred embodiment, a bead according to the invention comprises reflective particles in the form of flakes and having a ratio d/e equal to or greater than 10 selected in the group consisting of:

flake particles having at least two parallel faces that consist of a single material which is optically uniform; and flake particles that have a layered structure with at least two layers of material that are different optically preferably selected from pigments having a substrate and coating structure, or pigments that are multilayered without a substrate and their mixture, also called multilayer interference pigments, diffractive pigments, and mixtures thereof.

According to a preferred embodiment a bead according to the invention comprises particles in the form of flakes and having a ratio d/e equal to or greater than 10 selected in the group consisting of multilayer interference pigments and their mixture, preferably said multilayer interference pigments being selected from nacres, reflective interference particles, goniochromatic pigments and their mixture.

Preferably the Reflective Particles According to the Invention are Selected from Inorganic Particles Coated with Metallic (Poly)Oxides.

As examples of substrates which may be coated by poly(oxides), mica or synthetic fluorphologopite may be cited, preferably mica.

As examples of metallic (poly)oxides, mention may be made of: titanium dioxide, iron oxide, tin oxide, and their mixture, and preferably of at least titanium dioxide.

According to a particular embodiment, such an inorganic particle is a mica-titanium dioxide, a mica-titanium dioxide-tin oxide or a mica-titanium dioxide-iron oxide particle.

Flake Particles Having at Least Two Parallel Faces that Consist of a Single Material that is Optically Uniform As examples of flake particles having at least two parallel faces that consist of a single material that is optically uniform, mention may be made of: metal-effect pigments, such as metal flakes, e.g. flakes of aluminum or of metal-alloy, e.g. copper-zinc alloy; silica, synthetic mica, or glass particles; or transparent-effect pigments such as crystalline bismuth oxychloride or polycrystalline titanium dioxide.

As examples of metal pigments, mention may be made of aluminum, bronze, or copper powders that are coated with $SiO_2$ and sold under the trade name VISIONAIRE by ECKART.

As examples of glass flakes, mention may be made of compositions sold under the name SILKYFLAKE by Nippon Sheet Glass.

As an example of bismuth oxychloride-based pigment, mention may be made of BIRON pigments sold by Merck, and PEARL compositions sold by FARMAQUIMIA.

Multilayer Interference Pigment

The expression "multilayer interference pigment" means a pigment that is capable of producing a color by an interference phenomenon between the light rays reflected by a plurality of superposed layers of different refractive indices, in particular a succession of layers of high and low refractive indices.

Any multilayer interference pigment may be envisaged.

Any color may be produced by the multilayer interference pigment, e.g. optionally being of dominant wavelength lying in the range 580 nm to 650 nm.

The composition may include a single multilayer interference pigment or a plurality of multilayer interference pigments having different dominant wavelengths.

The multilayer interference pigment may comprise a substrate (also known as a core) that is covered, on at least one face, by one or more layers made of materials and thicknesses that are selected such that a color is produced by interference.

Layers of the interference pigment may optionally surround the substrate which may present an optionally flat shape.

When reflective particles have a multilayer structure, they may comprise a natural or synthetic substrate, particularly a synthetic substrate at least partially coated by at least one layer of a reflective material in particular a layer made of metal or metallic material. The substrate may be made of a single material or a plurality of materials; it may be mineral or organic.

The substrate may include natural glass, ceramic, graphite, metal oxide, alumina, silica, silicates, particularly alumina-silicates, boro-silicates, synthetic mica, or their mixture.

The substrate may include natural mica, synthetic mica, glass, alumina, silica, or even any metal, alloy, or metal oxide.

The type of substrate could be selected as a function of the glossiness desired. For example, for a very glossy result, a substrate made of glass or of metal could be preferred.

The interference pigment may include more than four layers of different refractive indices.

The size of the particles of the multilayer interference pigment, given by the mean grain size at half the population, also referred to as $D_{50}$, lies in the range 1 μm to 2000 μm, for example, better in the range 5 μm to 2000 μm.

The proportion of multilayer interference pigment is greater than 7%, for example, and lies in the range 7% to 20%, for example, for a non-powder, liquid, or cast composition, e.g. a composition in stick form, and in the range 40% to 95%, for example, for a loose- or compacted-powder composition.

Nacres are examples of suitable multilayer interference pigments.

Nacres

The term "nacre" means colored particles of any form, which may optionally be iridescent, as produced in the shells of certain mollusks, or which are synthesized, and which exhibit a "pearlescent" coloring effect by optical interference.

Examples of nacres that may be mentioned are nacre pigments such as mica titanium coated with iron oxide, mica coated with bismuth oxychloride, mica titanium coated with chromium oxide, mica titanium coated with an organic colorant in particular, and nacre pigments based on bismuth oxychloride. "Mica titanium" means mica coated with $TiO_2$.

They may also be particles of mica on the surface of which at least two successive layers of metal oxides and/or organic coloring substances have been superimposed.

The nacres may have a yellow, pink, red, bronze, orangey, brown, gold, and/or coppery color or glint.

Illustrative examples of nacres suitable for being introduced as a multilayer interference pigment and that may be mentioned are gold color nacres, in particular those sold by ENGELHARD under the trade names Brillant gold 20 212G (Timica), Gold 222C (Cloisonne), Sparkle gold (Timica), Gold 4504 (Chromalite), and Monarch gold 233X (Cloisonne); bronze nacres, in particular those sold by MERCK under the trade names Bronze fine (17384) (Colorona) and Bronze (17353) (Colorona), and by ENGELHARD under the trade name Super bronze (Cloisonne); orange nacres in particular those sold by ENGELHARD under the trade names Orange 363C (Cloisonne) and Orange MCR 101 (Cosmica), and by MERCK under the trade names Passion orange (Colorona) and Matte orange (17449) (Microna); brown-tinted nacres in particular those sold by ENGELHARD under the trade names Nu-antique copper 340XB (Cloisonne) and Brown CL4509 (Chromalite); nacres with a copper glint in particular those sold by ENGELHARD under the trade name Copper 340A (Timica); nacres with a red glint, in particular those sold by MERCK under the trade name Sienna fine (17386) (Colorona); nacres with a yellow glint, in particular those sold by ENGELHARD under the trade name Yellow (4502) (Chromalite); red-tinted nacres with gold glints, in particular those sold by ENGELHARD under the trade name Sunstone G012 (Gemtone); pink nacres, in particular those sold by ENGELHARD under the trade name Tan opale G005 (Gemtone); black nacres with a gold glint, in particular those sold by ENGELHARD under the trade name Nu antique bronze 240 AB (Timica); blue nacres, in particular those sold by MERCK under the trade name Matte blue (17433) (Microna); white nacres with silvery glints, in particular those sold by MERCK under the trade name Xirona Silver; and orange-pink green-gold highlight nacres in particular those sold by MERCK under the trade names Indian summer (Xirona); and mixtures thereof.

Glass-based interference particles such as Ronastar sold by MERCK or synthetic mica-based interference particles such as Sunshine sold by SUN CHEMICAL or PROMINENCE sold by NIKON KOKEN and their mixture may also be cited.

By way of example, multilayer interference pigments presenting magnetic properties are those sold under the trade names: COLORONA BLACKS TAR BLUE, COLORONA BLACKSTAR GREEN, COLORONA BLACKSTAR GOLD, COLORONA BLACKSTAR RED, CLOISONNE NU ANTIQUE SUPER GREEN, MICRONA MATTE BLACK (17437), MICA BLACK (17260), COLORONA PATINA SILVER (17289), and COLORONA PATINA GOLD (117288) by MERCK; or indeed: FLAMENCO TWILIGHT RED, FLAMENCO 25 TWILIGHT GREEN, FLAMENCO TWILIGHT GOLD, FLAMENCO TWILIGHT BLUE, TIMICA NU ANTIQUE SILVER 110 AB, TIMICA NU ANTIQUE GOLD 212 GB, TIMICA NU-ANTIQUE COPPER 340 AB, TIMICA NU ANTIQUE BRONZE 240 AB, CLOISONNE NU ANTIQUE GREEN 828 CB, CLOISONNE NU ANTIQUE BLUE 626 CB, GEMTONE MOONSTONE G 004, CLOISONNE NU ANTIQUE RED 424 CB, CHROMA-LITE BLACK (4498), CLOISONNE NU ANTIQUE ROUGE FLAMBE (code 440 XB), CLOISONNE NU ANTIQUE BRONZE (240 XB), CLOISONNE NU ANTIQUE GOLD (222 CB), and CLOISONNE NU ANTIQUE COPPER (340 XB) by ENGELHARD.

The multilayer interference pigment may also be selected from the reflective interference particles.

Reflective Interference Particles

These particles may be selected from particles of synthetic substrate at least partially coated with at least one layer of at least one metal oxide selected, for example, from oxides of titanium, in particular $TiO_2$, of iron, in particular $Fe_2O_3$, of tin, or of chromium, barium sulfate, and the following materials: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

More precisely as example of particle in the form of flakes having a layer structure, the following may be cited: particle in the form of flakes made of natural or synthetic mica coated with at least one layer of metal oxide, chosen from oxides of titanium, in particular $TiO_2$, of iron, in particular $Fe_2O_3$, of tin, or of chromium, barium sulfate, and the following materials: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$, and mixtures or alloys thereof.

Examples of such particles that may be mentioned are particles comprising a substrate of synthetic mica coated with titanium dioxide, or glass particles coated either with brown iron oxide, titanium oxide, tin oxide, or one mixture thereof such as those sold under the trade name REFLECKS® by ENGELHARD.

Other examples of such particles that may be mentioned are particles comprising a mineral substrate coated with a metal layer, particles having a boro-silicate substrate coated with silver sold under the trade name METASHINE® by Nippon Sheet Glass.

The multilayer interference pigment may also be a goniochromatic pigment.

Goniochromatic Pigment

The term "goniochromatic pigment" as used in the context of the present invention means a pigment that makes it possible, when the composition is spread on a substrate, to obtain a color path in the a*b* plane of the 1976 CIE color space which corresponds to a variation Dh° of the hue angle h° of at least 20° when the angle of observation is varied relative to the normal in the range 0 to 80° for light at an angle of incidence of 45°.

By way of example, the color path may be measured by means of a spectrogonioreflectometer, from INSTRUMENT SYSTEMS and referenced GON 360 GONIOMETER, after the composition has been spread in the fluid state to a thickness of 300 μm by means of an automatic spreader on a contrast card from ERICHSEN and referenced Typ 24/5, the measurements being performed on the black background of the card.

The goniochromatic pigment may, for example, be selected from multilayer interference structures and liquid crystal coloring agents.

By way of example, a multilayer structure may comprise at least two layers, each layer being produced, for example, from at least one material selected from the group constituted by the following materials: $MgF_2$, $CeF_3$, ZnS, ZnSe, Si, $SiO_2$, Ge, Te, $Fe_2O_3$, Pt, Va, $Al_2O_3$, MgO, $Y_2O_3$, $S_2O_3$, SiO, $HfO_2$, $ZrO_2$, $CeO_2$, $Nb_2O_5$, $Ta_2O_5$, $TiO_2$, Ag, Al, Au, Cu, Rb, Ti, Ta, W, Zn, $MoS_2$, cryolite, alloys, polymers, and combinations thereof.

The multilayer structure may optionally be symmetrical with respect to a central layer as regards the chemical nature of the stacked layers.

Depending on the thickness and nature of the various layers, different effects are obtained.

Examples of symmetrical multilayer interference structures are as follows: $Fe_2O_3/SiO_2/Fe_2O_3/SiO_2/Fe_2O_3$, a pigment having this structure being sold under the trade name SICOPEARL by BASF; $MoS_2/SiO_2$/mica-oxide/$SiO_2MoS_2$; $Fe_2O_3/SiO_2$/mica-oxide/$SiO_2/Fe_2O_3$; $TiO_2/SiO_2/TiO_2$ and $TiO_2/Al_2O_3/TiO_2$, pigments having these structures being sold under the trade name XIRONA by MERCK (Darmstadt).

By way of example, liquid crystal coloring agents comprise silicones, or cellulose ethers onto which mesomorphic groups have been grafted. Examples of suitable liquid crystal goniochromatic particles are those sold by CHENIX, and those sold under the trade name HELICONE® HC by WACKER.

Suitable goniochromatic pigments are some nacres; pigments having effects on synthetic substrates, in particular alumina, silica, borosilicate, iron oxide, or aluminum type substrates; or interference flakes coming from a polyterephthalate film.

The material may further contain dispersed goniochromatic fibers. Such fibers could present a length that is less than 80 µm, for example.

Diffracting Pigment

The term "diffracting pigment" as used in the present invention means a pigment which is capable of producing a color variation depending on the angle of observation when illuminated with white light due to the presence of a structure which diffracts light.

Such a pigment is also sometimes termed a holographic pigment or rainbow effect pigment.

A diffracting pigment may comprise a diffraction matrix capable, for example, of diffracting an incident ray of monochromatic light in predetermined directions.

The diffraction matrix may comprise a periodic motif, in particular a line, the distance between two adjacent motifs being of the same order of magnitude as the wavelength of the incident light.

When the incident light is polychromatic, the diffraction matrix separates the various spectral components of the light and produces a rainbow effect. Concerning the structure of diffracting pigments, reference should be made to the article "*Pigments Exhibiting Diffractive Effects*" by Alberto Argoitia and Matt Witzman, 2002, Society of Vacuum Coaters, 45$^{th}$ Annual Technical Conference Proceedings, 2002, the contents of which are hereby incorporated by reference.

The diffracting pigment may be produced with motifs having different profiles, in particular triangular, symmetrical or unsymmetrical, crenellated, with a constant or non constant width, sinusoidal, or stepped.

The spatial frequency of the matrix and the motif depth will be selected as a function of the desired degree of separation of the various orders. As an example, the frequency may lie in the range 500 to 3000 lines per mm.

Preferably, the particles of diffracting pigment each have a flattened form, in particular in the form of a platelet. The same pigment particle may comprise two crossed diffraction matrices, which may or may not be perpendicular, and may or may not have the same spacing.

The diffracting pigment may have a multi-layered structure comprising a layer of reflective material, covered on at least one side by a layer of a dielectric material. This layer may provide the diffracting pigment with better rigidity and durability. The dielectric material may thus, for example, be selected from the following materials: $MgF_2$, $SiO_2$, $Al_2O_3$, $AlF_3$, $CeF_3$, $LaF_3$, $NdF_3$, $SmF_2$, $BaF_2$, $CaF_2$, LiF, and combinations thereof.

The reflective material may, for example, be selected from metals and their alloys and also from non-metallic reflective materials. Metals which may be mentioned include Al, Ag, Cu, Au, Pt, Sn, Ti, Pd, Ni, Co, Rd, Nb, Cr, and their materials, combinations or alloys. Such a reflective material may alone constitute the diffracting pigment which is then a monolayer.

In a variation, the diffracting pigment may comprise a multi-layered structure comprising a substrate of a dielectric material covered on at least one side by a reflective layer, or even completely encapsulating the substrate.

A layer of a dielectric material may also cover the reflective layer or layers. The dielectric material used is thus preferably inorganic and may, for example, be selected from metal fluorides, metal oxides, metal sulfides, metal nitrides, metal carbides and combinations thereof. The dielectric material may be in the crystalline, semi-crystalline or amorphous state. The dielectric material in this configuration may, for example, be selected from the following materials: $MgF_2$, SiO, $SiO_2$, $Al_2O_3$, $TiO_2$, WO, AlN, BN, $B_4C$, WC, TiC, TiN, $N_4Si_3$, ZnS, glass particles, diamond type carbons, and combinations thereof. In a variation, the diffracting pigment may be composed of a dielectric or preformed ceramic material such as a mineral in natural lamellae, for example mica peroskovite or talc, or synthetic lamellae formed from glass, alumina, $SiO_2$, carbon, an iron oxide/mica, mica coated with BN, BC, graphite, bismuth oxychloride, and combinations thereof.

Instead of a layer of a dielectric material, other materials which improve the mechanical properties may be suitable. Such materials may include silicone, metal silicides, semiconductor materials formed from elements from groups III, IV, and V, metals having a body-centered cubic crystal structure, Cermet compositions or materials, semiconductor glasses, and their various combinations. The diffracting pigment used may in particular be selected from those described in United States patent application US-2003/0031870 published on Feb. 13, 2003. A diffracting pigment may, for example, comprise the following structure: $MgF_2$/Al/$MgF_2$, a diffracting pigment having that structure being sold under the trade name SPECTRAFLAIR 1400 Pigment Silver by FLEX PRODUCTS, or SPECTRFLAIR 1400 Pigment Silver FG. The proportion by weight of $MgF_2$ may be in the range 80% to 95% of the total weight of the pigment. Other diffracting pigments are sold under the trade names METALURE® PRISMATIC by ECKART®.

Other possible structures are Fe/Al/Fe or Al/Fe/Al.

The dimension of the diffracting pigment may, for example, be in the range 5 µm to 200 µm, better in the range 5 µm to 100 µm, for example in the range 5 µm to 30 µm. The thickness of the particles of diffracting pigment may be 3 µm or less, preferably 2 µm, for example of the order of 1 µm.

II. Methods for Preparing Microcapsules

The microcapsules may be produced by a process including:

preparing an aqueous solution containing water and a first hydrophilic polymer;

dispersing reflective particles in the aqueous solution;

forming an inner layer on a core with the aqueous solution in which the reflective particles are dispersed;

forming an intermediate layer on the inner layer with an intermediate layer solution containing water, a second hydrophilic polymer, and a pigment; and forming an outer layer on the intermediate layer with an outer layer solution containing water and a third hydrophilic polymer.

The hydrophilic polymer, the reflective particles, the pigment, and the core can be any one or combination of those listed above. The properties such as the size of the core or the reflective particles can be the same as those described above. The first, second, and third hydrophilic polymers can be the same or different.

The amount of each of water, the hydrophilic polymer, and the core can be any amount determined by a person of ordinary skill in the art. For example, the aqueous solution can be prepared by dissolving 100-200 weight parts of the hydrophilic polymer in 7,000-16,000 weight parts of water, and 500-1,500 weight parts of the reflective particles can be added to the solution. In another example, a mixture of water and alcohol can be used instead of water. For example, 500-1,000 g of the core is coated with a spray drying process. For example, the solution for the intermediate layer can contain 2,000-5,000 weight parts of water and 2-10 weight parts of the lipid, and 10-40 weight parts of the hydrophilic polymer. For example, the solution for the outer layer can contain 300-500 weight parts of water, 1-3 weight parts of the hydrophilic polymer, and optionally 0.5-1.5 weight parts of the lipid.

The aqueous solution can be prepared with an appropriate way. For example, the hydrophilic polymer can be dissolved in the solution at 50-100° C., preferably 75-99° C., for example, 95° C.

The aqueous solution can be prepared by mixing two solutions, each of which contains different hydrophilic solutions containing, for example, different hydrophilic polymers. For example, one contains a starch derivative, and another contains polyvinyl alcohol. The aqueous solution can contain another aqueous solvent, for example, a lower alcohol such as ethanol. At least one of the layers can contain a lipid such as one of those listed above.

The coating step can be carried out with a spray drying process.

Several methods known to the man skilled in the art within the coating or encapsulation domain, including spray drying, pelletization, granulation, coating, etc. may also be used. Spray drying processes may be carried out by any method e.g. tangential, bottom or top spray drying. It may also be combined with a drying in a fluidized bed process. These alternatives may further be combined in order to obtain microcapsules having the required properties.

Preferably at least one outer layer, more preferably all outer layers are obtained by a combination of one or several of these alternatives: tangential, bottom or top spray drying optionally combined with a fluidized bed process.

For example, the microcapsules may be obtained by a method comprising mixture of the compounds (reflective particles, other optional actives, polymers, solvents) and drying to form capsules as disclosed in WO01/35933 and WO2011/027960, or a method comprising granulation and coating by spray drying as disclosed in FR2841155, or by fluidized bed technology, which has been used in the food and pharmaceutical industry for a long time for coating and encapsulating ingredients. As an example may be cited WO2008/139053, which concerns the preparation of spheroid multilayer capsules comprising a core of sugar and concentric layers of pharmaceutical actives. Fixation of pharmaceutical actives on the core is achieved by impregnation, pulverization or projection, and then the 1$^{st}$ layer is dried before application of a second one.

Fluid Bed Process

Fluid bed process is disclosed for example in Teunou et al. (Fluid-Bed Coating, Poncelet, 2005, D. *Food Science and Technology* (Boca Raton, Fla., United States), Volume 146 Issue Encapsulated and Powdered Foods, Pages 197-212). A specific feature of the fluid bed process is that it leads to coated particles wherein the core is well encapsulated, compared to spray drying, which leads to a matrix with the core material randomly dispersed in a polymer.

In a preferred embodiment, the microcapsules are obtained by fluid bed process.

According to this embodiment, preferably at least one layer of the microcapsules is obtained by fluid bed process.

In a particular embodiment, the outer layer is obtained by fluid bed process.

In another particular embodiment at least one inner layer is obtained by fluid process.

At least one layer, most preferably, all layers are obtained by fluid bed process.

The man skilled in the art knows how to adjust air quantity, liquid quantity and temperature allowing to reproduce a microcapsule according to the invention.

Preferably a fluid bed process implemented according to the invention includes Würster process and/or tangential spray process. Such a process allows, contrary to a pelletization process, to prepare spherical capsules with a core surrounded by one or more circumferential layers.

When the whole process for preparing the layers surrounding the core of the microcapsules according to the invention is carried out by fluid bed process, the microcapsule layers are advantageously regular, concentric and present a homogenous thickness.

Advantageously this water acts as a swelling agent or as a softening agent towards these microcapsules without breaking them. The microcapsules are not inert when placed in water either they swell: their diameter significantly increases with an optional softening of the microcapsules, or the microcapsules significantly soften without increasing of the diameter, they become more malleable and easier to break when applied onto the skin.

Water is able to act on the softening kinetics of the microcapsules and more particularly it allows to obtain a good balance between softening kinetics and hardness.

As a consequence, water is particularly advantageous for softening these microcapsules suitable for the present invention, in an appropriate way, since it plays a role on softening kinetics of said microcapsules.

Said microcapsules are preferably deformable in the presence of an aqueous phase, notably in the presence of water.

According to this embodiment of the invention, composition comprise water in a content ranging from 30% to 99% by weight, preferably from 40% to 95% more preferably from 50% to 90% by weight relative to the total weight of the said composition.

Optionally it also comprises at least one compound chosen from polyols, glycols and $C_2$-$C_8$ monoalcohols, and mixtures thereof.

Said polyol is preferably selected from the group consisting in glycerol, glycols, preferably propylene glycol, butylene glycol, pentylene glycol, hexylene glycol, dipropylene glycol, diethylene glycol, glycol ethers, preferably mono-, di- or tripropylene glycol of alkyl($C_1$-$C_4$)ether or mono-, di- or triethylene glycol of alkyl($C_1$-$C_4$)ether, and mixtures thereof.

The invention is illustrated in greater detail by the examples according to the invention described below. Unless otherwise mentioned, the amounts indicated are expressed as mass percentages of active material.

EXAMPLES

Some examples of the present invention are provided below. These examples are illustrative, but not limiting the scope of the present invention. Reasonable variations can be made herein without departing from the scope of the present invention.

Different examples of preparation of microcapsules according to the invention are here below described for illustrating the invention.

Example 1a

Mannitol (spray dried mannitol: Pearlitol 100SD) is used as a core.

To a solution of 7,382 g of water and 66 g of Starch derivative (Structure XL) is completely dissolved at room temperature to prepare a first solution. To a mixed solutions of 418 g of water with 22 g of Polyvinyl alcohol (SELVOL™ (Celvol®) Polyvinyl alcohol 205S) is completely dissolved at 95° C. to prepare a second solution. These solutions are combined to form a mixture. At this stage, 1,080 g of Syncrystal almond (a reflective particle) is added to the mixture and well dispersed with a homogenizer (3000 rpm, 20 min.) to prepare an inner charged coating solution.

832 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This yields particles with the size range of approximately 75 µm~212 µm.

Thereafter, to a solution of 5,000 g of water, 32.8 g of cornstarch and 6.6 g of hydrogenated lecithin (Lipoid P75-3) are added and dissolved at 40° C. To the resulting mixture, 1,300 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 2.0 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. The resulting coated particles produced according to this process are obtainable with a size ranging from approximately 75 µm~250 µm.

Example 1b

Mannitol (spray dried mannitol: Pearlitol 100SD) is used as a core.

To a solution of 14382.5 g of water and 130 g of Starch derivative (Structure XL) is completely dissolved at room temperature to produce a first solution. To a mixed solution of 617.5 g of water with 32.5 g of Polyvinyl alcohol (SELVOL™ (Celvol®) Polyvinyl alcohol 205S) is completely dissolved at 95° C. to produce a second solution. After mixing the first and second solutions, 1080 g of Timica® Terra White(a reflective particle) is added and well dispersed with a homogenizer (3000 rpm, 20 min.) to prepare an inner charged coating solution.

537.5 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process yields particles with the size range 75 µm~212 µm.

Thereafter, to a solution of 2200 g of water, 14 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 2.0 g of cornstarch is dissolved in 400 g of water at 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 µm~250 µm.

Example 1c

Mannitol (spray dried mannitol: Pearlitol 100SD) is used as a core.

132 g of Starch derivative (Structure XL) is completely dissolved in 11,837 g of water at room temperature to produce a first solution. 33 g of Polyvinyl alcohol (SELVOL™ (Celvol®) Polyvinyl alcohol 205S) is completely dissolved in 627 g of water at 95° C. to produce a second solution. After mixing the first and second solutions, 1800 g of Syncrystal almond (a reflective particle) is added and well dispersed with a homogenizer (3000 rpm, 20 min.) to prepare an inner charged coating solution.

535 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This method generates particles with a size range of approximately 75 µm~212 µm.

Thereafter, to a solution of 2600 g of water, 14.0 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 1.2 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 µm~250 µm.

Example 1d

Mannitol (spray dried mannitol: Pearlitol 100SD) is used as a core.

66 g of Starch derivative (Structure XL) is completely dissolved in 7,382 g of water at room temperature to produce a first solution. 22 g of Polyvinyl alcohol (SELVOL™ (Celvol®) Polyvinyl alcohol 205S) is completely dissolved in 421 g of water at 95° C. to produce a second solution. After mixing the first and second solutions, Syncrystal almond (a reflective particle) is added and well dispersed with a homogenizer (3000 rpm, 20 min.) to prepare an inner charged coating solution.

832 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process generates particles with the size range of approximately 75 μm~212 μm.

Thereafter, to a solution of 5200 g of water, 27.6 g of cornstarch and 5.6 g of hydrogenated lecithin (Lipoid P75-3) are added and dissolved at 40° C. To the resulting mixture, 1100 g of titanium dioxide particles (HOMBITAN FF-PHARMA) are added and well dispersed with a homogenizer (with 3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 2.0 g of cornstarch is dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles produced according to this method are obtainable with a size range of approximately 75 μm~250 μm.

Example 2a

Mannitol (spray dried mannitol: Pearlitol 100SD) is used as a core.

144 g of Starch derivative (Structure XL) is completely dissolved at room temperature in 14,566 g of water to produce a first solution. 36 g of polyvinyl alcohol (SELVOL™ (Celvol®) Polyvinyl alcohol S325) is completely dissolved in 684 g of water at 95° C. to produce a second solution. After mixing the first and second solution, 1800 g of Colorona® Oriental Beige (a reflective particle) is added and well dispersed with a homogenizer (3000 rpm, 20 min.) to prepare an inner charged coating solution.

520 g of Mannitol is introduced into a fluidized bed coating system (Glatt GPCG 1, bottom spray) as a seed and subjected to a coating at 500 ml/h of feeding rate of inner layer charged solution to obtain particles having a mannitol core coated with an inner charged layer. This process yields articles with a size range of approximately 75 μm~212 μm.

Thereafter, to a solution of 2600 g of water, 14.0 g of cornstarch and 2.8 g of hydrogenated lecithin (Lipoid P75-3) are added and dissolved at 40° C. To the resulting mixture, 560 g of titanium dioxide particles (HOMBITAN FF-PHARMA) are added and well dispersed with a homogenizer (3000 rpm, 20 min.) to prepare a titanium dioxide particle coating solution.

A coating with the resulting titanium dioxide particle coating solution is realized by a fluidized bed process to obtain particles having an inner charged layer coated with a titanium dioxide particle layer.

Then, 1.2 g of cornstarch and 0.6 g of hydrogenated lecithin (Lipoid P 75-3) are dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. This method generates coated particles with a size range of approximately 75 μm~250 μm.

Example 2b

Mannitol (spray dried mannitol: Pearlitol 100SD) is used as a core.

5750.0 g of ethanol, 75.0 g of ethyl cellulose (Ethocel standard 10 premium) and 150 g of FCC (SE-06) are completely dissolved in 1437.5 g of water at room temperature. To the resulting mixture, 1800 g of Colorona® Oriental Beige (a reflective particles) are added and well dispersed with a homogenizer (3000 rpm, 20 min) to prepare an inner charged coating solution.

469.5 g of Mannitol is introduced into a fluidized bed coating system (Glatt GPOG 1, bottom spray) as a seed and subjected to a coating at 500 mk/h of feeding rate of the inner color charged solution to obtain particles having a mannitol core coated with an inner charged layer. This process yields particles with the size range of approximately 75 μm~212 μm.

Thereafter, to a solution of 2400 g of water, 14.0 g of cornstarch and 2.8 g of hydrogenated lecithin (Lipoid P75-3) are added and dissolved at 40° C. To the resulting mixture, 560 g of titanium dioxide particles (KRONOS1171) are added and well dispersed with a homogenizer (3000 rpm, 20 min.) to prepare a titanium dioxide particle coating solution.

A coating with the resulting titanium dioxide particle coating solution is generated by a fluidized bed process to obtain particles having an inner charged layer coated with a titanium dioxide particle layer.

Then, 1.2 g of cornstarch and 0.6 g of hydrogenated lecithin (Lipoid P75-3) are dissolved in 400 g of water art 95° C. to prepare an outer layer coating solution, which is coated onto the above titanium dioxide particle layer to obtain a microcapsule encapsulating in its inner layer, surrounding the core in mannitol, the reflective particle, and also having a titanium dioxide particle layer coated with an outer layer. Coated particles prepared according to this method are obtainable with the size range of approximately 75 μm~250 μm.

Example 3

By using the ingredients and contents described in the below table, a microcapsule having a core and 2 layers is prepared by the procedure provided in Example 1 or 2:

(1) reflective particle F (2) Ingredients: Core seed—reflective particle inner layer—$TiO_2$ particle layer

| Core | Mannitol | 16.45% |
| --- | --- | --- |
| $1^{st}$ layer | reflective particle F | 50.0% |
|  | Lecithin | 0.5% |
|  | Corn Starch binder | 2.0% |
| $2^{nd}$ layer | Titanium dioxide | qsp. 100% |
|  | Lecithin | 0.2% |
|  | Corn Starch binder | 0.8% |

Percentages indicate weight percent relative to the total microcapsule weight.

Example 4

By using the ingredients and contents described in the below table, a microcapsule having a core and 3 layers is prepared by the procedure provided in Example 1 or 2:
(1) reflective particle C
(2) Ingredients: Core seed—reflective particle inner layer—TiO$_2$ particle layer—outer color layer

| Core | Mannitol | 6.5% |
|---|---|---|
| 1$^{st}$ layer | reflective particle C | 17.8% |
| | Sunpuro Yellow | 2.00% |
| | Lecithin | 5.0% |
| | Eudragit RSPO | 4.0% |
| 2$^{nd}$ layer | Titanium dioxide | qsp. 100% |
| | Lecithin | 5.0% |
| | Eudragit RSPO | 4.0% |
| 3$^{rd}$ layer | D&C Red30 | 0.8% |
| | Cornstarch binder | 0.4% |

Percentages indicate weight percent relative to the total microcapsule weight.

Example 5

By using the ingredients and contents described in the below table, a microcapsule having a core and 2 layers is prepared by the procedure provided in Example 1 or 2:
(1) reflective particle A
(2) Ingredients: Core seed—reflective particle inner layer—TiO$_2$ particle layer

| Core | Mannitol | 17.8% |
|---|---|---|
| 1$^{st}$ layer | Reflective particle A | 19.8% |
| | Lecithin | 0.2% |
| | Corn Starch binder | 0.8% |
| 2$^{nd}$ layer | Titanium dioxide | qsp. 100% |
| | Mannitol | 5.0% |
| | Corn Starch | 5.0% |
| | Lecithin | 0.3% |
| | Corn Starch binder | 1.2% |

Percentages indicate weight percent relative to the total microcapsule weight.

Example 6

By using the ingredients and contents described in the below table, a microcapsule having a core and 2 layers is prepared by the procedure provided in Example 1 or 2:
(1) Ingredients: Core seed—Reflective particle inner color layer—TiO$_2$ particle layer

| Core | Mannitol | 13.7% |
|---|---|---|
| 1$^{st}$ layer | Reflective particle D | 21.64% |
| | Lecithin | 0.20% |
| | Corn Starch Binder | 1.0% |
| 2$^{nd}$ layer | Titanium dioxide | qsp. 100% |
| | Lecithin | 0.3% |
| | Corn Starch Binder | 1.5% |

Percentages indicate weight percent relative to the total microcapsule weight.

Example 7

By using the ingredients and contents described in the below table, a microcapsule having a core and 3 layers is prepared by the procedure provided in Example 1 or 2:
(1) Reflective particle H
(2) Ingredients: Core seed—reflective particle inner layer—TiO$_2$ particle layer—Outer color layer

| Core | Mannitol | 16.81% |
|---|---|---|
| 1$^{st}$ layer | reflective particle H | 49.15% |
| | Lecithin | 0.29% |
| | Corn Starch Binder | 1.97% |
| 2$^{nd}$ layer | Titanium dioxide | qsp100%% |
| | Lecithin | 0.1% |
| | Corn Starch Binder | 0.49% |
| 3$^{rd}$ layer | Sunpuro Yellow | 1.0% |
| | Sunpuro Red | 0.2% |
| | Corn Starch Binder | 0.5% |

Percentages indicate weight percent relative to the total microcapsule weight.

Example 8

By using the ingredients and contents described in the below table, a microcapsule having a core and 3 layers is prepared by the procedure provided in Example 1 or 2:
(1) reflective particle H
(2) Ingredients: Core seed—reflective particle inner layer—TiO$_2$ particle layer—Outer color layer

| Core | Organic core | 4.0% | Cellulose | 1.12% |
|---|---|---|---|---|
| | | | Mannitol | 1.0% |
| | | | Zea Mays(corn) starch | 1.84% |
| | | | Hydrogenated Lecithin | 0.04% |
| 1$^{st}$ layer | reflective particle H | 55.0% | reflective particle | 55 |
| | Lecithin | 0.50% | Hydrogenated Lecithin | 0.50% |
| | Mannitol | 3.5% | Mannitol | 3.5% |
| | Corn Starch Binder | 2.0% | Zea Mays(corn) starch | 2.0% |
| 2$^{nd}$ layer | Titanium dioxide | qsp100%. | Titanium dioxide | qsp100%. |
| | Corn Starch | 3.62% | Zea Mays(corn) starch | 3.62% |
| | Cellulose | 9.0% | Cellulose | 9.0% |
| | Mannitol | 13.0% | Mannitol | 13.0% |
| | Lecithin | 0.25% | Hydrogenated Lecithin | 0.25% |
| | Corn Starch Binder | 1.8% | Zea Mays(corn) starch | 1.8% |
| 3$^{rd}$ Layer | Satin White | 1.8% | Synthetic Fluorphlogopite | 1.035% |
| | | | Tin oxide | 0.009% |
| | | | Titanium Dioxide | 0.756% |
| | D&C Red30 | 0.03% | Red30 Al. Lake | 0.03% |
| | Corn Starch Binder | 0.5% | Zea Mays(corn) starch | 0.5% |

Percentages indicate weight percent relative to the total microcapsule weight.

Example 9

By using the ingredients and contents described in the below table, a microcapsule having a core and 3 layers is prepared by the procedure provided in Example 1 or 2:
(1) reflective particle G
(2) Ingredients: Core seed reflective particle inner layer—TiO$_2$ particle layer—Outer color layer

| Core | Mannitol | 34.4% |
|---|---|---|
| 1$^{st}$ layer | reflective particle G | 50.0% |
| | Lecithin | 0.50% |
| | Mannitol | 4.0% |
| | Corn Starch Binder | 2.0% |

-continued

| | | | | |
|---|---|---|---|---|
| $2^{nd}$ layer | Titanium dioxide | qsp100% | | |
| | Lecithin | 0.1% | | |
| | Corn Starch Binder | 0.4% | | |
| $3^{rd}$ Layer | C. Monarch gold | 3.0% | | |
| | Corn Starch Binder | 0.6% | | |

Percentages indicate weight percent relative to the total microcapsule weight.

(3) Ingredient of each layer (in details):

| | | | | |
|---|---|---|---|---|
| Core | Organic core | 34.4% | *Zea Mays*(corn) Starch | 14.3% |
| | | | Mannitol | 10.5% |
| | | | Cellulose | 9.6% |
| $1^{st}$ layer | reflective particle E | 50.0% | reflective particle | 50 |
| | Lecithin | 0.50% | Hydrogenated Lecithin | 0.50% |
| | Mannitol | 4.0% | Mannitol | 4.0% |
| | Corn Starch Binder | 2.0% | *Zea Mays*(corn) Starch | 2.0% |
| $2^{nd}$ layer | Titanium dioxide | qsp. 100% | Titanium dioxide | qsp. 100% |
| | Lecithin | 0.1% | Hydrogenated Lecithin | 0.1% |
| | Corn Starch Binder | 0.4% | *Zea Mays*(corn) Starch | 0.4% |
| $3^{rd}$ Layer | C. Monarch gold | 3.0% | Mica | 1.575% |
| | | | Titanium Dioxide | 1.29% |
| | | | Iron oxide Red | 0.12% |
| | | | Tin Oxide | 0.015% |
| | Corn Starch Binder | 0.6% | *Zea Mays*(corn) Starch | 0.6% |

Percentages indicate weight percent relative to the total microcapsule weight.

Example 10

By using the ingredients and contents described in the below table, a microcapsule having a core and 2 layers is prepared by the procedure provided in Example 1 or 2:

(1) Ingredients: Core seed—reflective particle layer—Outer color layer

| | | |
|---|---|---|
| Core | Mannitol | 27.85% |
| $1^{st}$ layer | reflective particle I | qsp. 100% |
| | Lecithin | 0.5% |
| | Corn Starch Binder | 1.5% |
| $2^{nd}$ layer | D&C Red30 | 0.145% |
| | Satin White | 4.55% |
| | Corn Starch Binder | 0.3% |

Percentages indicate weight percent relative to the total microcapsule weight.

(2) Ingredient of each layer (in details):

| | | | | |
|---|---|---|---|---|
| Core | Mannitol | 27.85% | Mannitol | 27.85% |
| $1^{st}$ layer | reflective particle B | qsp. 100% | reflective particle | qsp. 100% |
| | Lecithin | 0.5% | Lecithin | 0.5% |
| | Corn Starch Binder | 1.5% | Corn Starch Binder | 1.5% |
| $2^{nd}$ layer | D&C Red30 | 0.145% | D&C Red30 | 0.145% |
| | Satin White Sunshine Fine White | 4.55% | Synthetic Fluorphlogopite | 2.66% |
| | | | Tin oxide | 0.023% |
| | | | Titanium Dioxide | 1.867% |
| | Corn Starch Binder | 0.3% | Corn Starch Binder | 0.3% |

Percentages indicate weight percent relative to the total microcapsule weight.

Example 11

By using the ingredients and contents described in the below table, a microcapsule having a core and 3 layers is prepared by the procedure provided in Example 1 or 2:

1. reflective particle E
2. Ingredients: Core seed—reflective particle inner layer—TiO2 particle layer—Outmost shell

| | | | | |
|---|---|---|---|---|
| Core | Organic core | 4.0% | Cellulose | 1.0% |
| | | | Mannitol | 1.0% |
| | | | *Zea Mays*(corn) Starch | 2.0% |
| $1^{st}$ layer | reflective particle E | 50.0% | reflective particle | 50% |
| | Lecithin | 0.50% | Hydrogenated Lecithin | 0.50% |
| | Mannitol | 3.5% | Mannitol | 3.5% |
| | Corn Starch Binder | 2.0% | *Zea Mays*(corn) Starch | 2.0% |
| $2^{nd}$ layer | Titanium dioxide | qsp. 100% | Titanium dioxide | qsp. 100% |
| | Corn Starch | 2.0% | *Zea Mays*(corn) Starch | 2.0% |
| | Cellulose | 5.0% | Cellulose | 5.0% |
| | Mannitol | 6.5% | Mannitol | 6.5% |
| | Lecithin | 0.25% | Hydrogenated Lecithin | 0.25% |
| | Corn Starch Binder | 1.0% | *Zea Mays*(corn) Starch | 1.0% |
| $3^{rd}$ Layer | Iron oxide Red | 0.05% | Iron oxide Red | 0.05% |
| | Iron oxide Yellow | 0.01% | Iron oxide Yellow | 0.01% |
| | Cellulose | 5.0% | Cellulose | 5.0% |
| | Mannitol | 6.5% | Mannitol | 6.5% |
| | Corn Starch | 7.44% | *Zea Mays*(corn) Starch | 7.44% |
| | Lecithin | 0.25% | Hydrogenated Lecithin | 0.25% |
| | Corn Starch Binder | 1.0% | *Zea Mays*(corn) Starch | 1.0% |

Percentages indicate weight percent relative to the total microcapsule weight.

Example 12

By using the ingredients and contents described in the below table, a microcapsule, as shown in FIG. 1, having a core including notably mannitol and reflective particle, for instance B, is prepared by the procedure provided in Example 1 or 2:

| | | | | |
|---|---|---|---|---|
| Core | Lecithin | 0.9% | Hydrogenated Lecithin | 0.9% |
| | Mannitol | 18.9% | Mannitol | 18.9% |
| | Corn Starch Binder | 4.5% | *Zea Mays*(corn) Starch | 4.5% |
| | Reflective particle B | 75.6% | Reflective particle B | 75.6% |
| $1^{st}$ layer | Reflective particle B | 60.0% | Reflective particle B | 60.0 |
| | Lecithin | 0.04% | Hydrogenated Lecithin | 0.040% |
| | Mannitol | 15.0% | Mannitol | 15.0% |
| | Corn Starch Binder | 0.20% | *Zea Mays*(corn) Starch | 0.20% |
| $2^{nd}$ layer | Lecithin | 0.01% | Hydrogenated Lecithin | 0.01% |
| | Corn Starch Binder | 0.025% | *Zea Mays*(corn) Starch | 0.025% |

We claim:

1. A composition for cosmetic raw material comprising, at least one microcapsule containing at least one encapsulated releasable material,
   wherein the microcapsule comprises:
   a core comprising
   a reflective particle and
   an organic material selected from the group consisting of mannitol, erythritol, xylitol, sorbitol and a mixture thereof;

a layered coating surrounding the core comprising
a hydrophilic polymer selected from the group consisting of polysaccharide, starch or a derivative thereof;
a lipid based material selected from the group consisting of an amphiphilic compound, a phospholipid, phosphoacylglycerol and hydrogenated lecithin; and
a reflective particle which may be same or different from the reflective particle contained in the core; and
an outer layer comprising a hydrophilic polymer;
wherein the reflective particle is in the form of flakes having a ratio d/e greater than 10,
wherein d is a greatest dimension and e is a thickness of the reflective particle, and
wherein the microcapsule comprises between 30 and 80% by weight of reflective particle relative to the weight of the microcapsule, and
wherein the microcapsule is prepared by a method comprising:
preparing an aqueous solution containing water and a first hydrophilic polymer;
dispersing reflective particles in the aqueous solution;
forming an inner layer on the core with the aqueous solution in which the reflective particles are dispersed;
forming an intermediate layer on the inner layer with an intermediate layer solution containing water, a second hydrophilic polymer, and a pigment; and
forming the outer layer on the intermediate layer with an outer layer solution containing water and a third hydrophilic polymer,
provided that the aqueous solution does not include any hydrophobic solvent.

2. The composition of claim 1,
wherein the hydrophilic polymer, the reflective particles, the pigment, and the core can be any one or combination of those listed above;
wherein the size of the core or the reflective particles can be the same as those listed above;
wherein the first, second, and third hydrophilic polymers can be same or different;
wherein the amount of each of water, the hydrophilic polymer, and the core can be any amount determined by a person of ordinary skill in the art; and
wherein coating can be carried out with a spray drying process.

3. The composition of claim 2,
wherein the aqueous solution can be prepared by dissolving 100-200 weight parts of the hydrophilic polymer in 7,000-16,000 weight parts of water, and 500-1,500 weight parts of the reflective particles can be added to the solution.

4. The composition of claim 2,
wherein a mixture of water and alcohol can be used instead of water.

5. The composition of claim 2,
wherein the aqueous solution can be prepared with an appropriate way.

6. The composition of claim 5,
wherein the aqueous solution can be prepared by mixing two solutions, each of which contains different hydrophilic solutions containing different hydrophilic polymers.

* * * * *